US00PP11421P

United States Patent [19]

Austin

[11] Patent Number: Plant 11,421

[45] Date of Patent: Jun. 20, 2000

[54] SHRUB ROSE PLANT NAMED 'AUSHAM'

[75] Inventor: David C. H. Austin, Wolverhampton, United Kingdom

[73] Assignee: David Austin Roses Limited, Wolverhampton, United Kingdom

[21] Appl. No.: 09/168,298

[22] Filed: Oct. 7, 1998

[51] Int. Cl.[7] ..... A01H 5/00

[52] U.S. Cl. ..... Plt./107

[58] Field of Search ..... Plt./107, 102, 148, Plt./149

*Primary Examiner*—Howard J. Locker

*Attorney, Agent, or Firm*—Klarquist Sparkman Campbell Leigh & Whinston, LLP

[57] ABSTRACT

A shrub rose plant having disease resistance; strong growth; pink blooms of an old-fashioned shape; and the ability to repeat flower well through the summer.

1 Drawing Sheet

The present invention relates to a new and distinct variety of shrub rose plant of the *Rosa hybrida* class which was originated by me by crossing the variety 'Ausblush', unpatented, with an unnamed seedling.

The primary objective of this breeding was to produce a new shrub rose variety having a disease resistant, strong-growing plant, with pink blooms of an old-fashioned shape, that repeat flowers well throughout the summer. The objective was substantially achieved, along with other desirable improvements, as evidenced by the following unique combination of characteristics that are outstanding in the new variety and that distinguish it from its parents, as well as from all other varieties of which I am aware:

1. Sturdy, compact growth;
2. Full, rounded pink flowers;
3. Very good disease resistance; and
4. Repeats flowers well.

Asexual reproduction of this new variety by budding, as performed at Albrighton, Wolverhampton, England, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'Ausblush' (unpatented).

*Pollen parent.*—Unnamed seedling of unknown parentage.

Classification:

*Botanical.*—*Rosa hybrida.*

*Commercial.*—Shrub.

FLOWER

Observations made from specimens grown in a garden environment at Albrighton, Wolverhampton, England, Jul. 13, 1995.

Blooming habit: Continuous.

Bud:

*Size.*—¾ to 1¼ inches long when the petals start to unfurl.

*Form.*—The bud form is short, pointed ovoid.

*Color.*—When sepals first divide, bud color is Red Group 54A and Red Group 54C. When half blown, the upper sides of the petals are Red Group 55D (majority) and Red Group 36B, and the lower sides of the petals are Red Group 55C and Red Group 55D.

*Sepals.*—Color: Yellow-Green Group 144B. Surface texture: Upper side furry; underside smooth, waxy. There are three lightly appendaged sepals and two unappendaged sepals with hairy edges.

*Receptacle.*—Color: Yellow-Green Group 144A. Shape: Pitcher. Size: Medium, broad (about ⅝ to ⅜ inch×½ inch). Surface: Smooth.

*Peduncle.*—Length: Medium, averaging about 1½ to 2½ inches. Surface: Smooth, prickly. Color: Greyed-Purple Group 187D towards top, and Yellow-Green Group 146C towards base. Strength: Bending.

Bloom:

*Size.*—Medium. Average open size is 2½ inches.

*Borne.*—Several together in pyramidal clusters of 2–4, mostly 3 blooms.

*Stems.*—Normal strength. Average length is about 8 to 22 inches.

*Form.*—When first open: Bloom is cupped. Permanence: Outer petals curl back.

*Petalage.*—Number of petals under normal conditions: 108.

*Color.*—The upper sides of the petals are Red Group 56C and Red Group 56D. The reverse sides of the petals are Red Group 56B (majority) and Red Group 56C. The base of each petal is Yellow Group 5A at the very tip, gradually blending to Yellow Group 10C. The major color on the upper sides is Red Group 56C.

*Variegations.*—None.

*Discoloration.*—The general tonality at the end of the first day: Red Group 56D. At the end of the third day: Same, no fading.

*Fragrance.*—Moderate.

Petals:

*Texture.*—Leathery.

*Shape.*—Oval.

*Form.*—Moderately quilled towards center of flower.

*Arrangement.*—Irregular. Petaloids are few and small in the center.

*Persistence.*—Petals hang on and dry.

*Lastingness.*—On the plant: Fair, about 4 to 5 days. As a cut flower: Not tested.

Reproductive parts:

*Anthers.*—Size: Medium. Quantity: Many. Color: Yellow-Orange Group 15B. Arrangement: Partly tucked in calyx.

*Filaments.*—Color: Yellow Group 9B.

*Pollen.*—Color: Yellow-Orange Group 21A.

*Styles.*—Color: Top — Red Group 52A. Bottom — Green Group 149D.

*Stigmas.*—Color: Yellow-Orange Group 16C.

Form: Shrub.

Growth: Medium, upright, branching, fairly compact. Mature plant is four feet in height and three feet in width.

Foliage: Number of leaflets on normal mid-stem leaves: Five to seven.

*Size.*—Medium. (6 to 7 inches long×5 to 6 inches wide.)

*Quantity.*—Normal.

*Color.*—New foliage: Upper side: Green Group 137A with Greyed-Purple Group 183A blush. Lower side: Yellow-Green Group 147B with 183C blush. Old foliage: Upper side: Green Group 137A, but darker. Lower side: Yellow-Green Group 147B.

Leaflets:

*Shape.*—Elliptic.

*Texture.*—Upper side: Leathery, semi-glossy.

*Edge.*—Serrated.

*Serration.*—Single, small.

*Petiole rachis.*—Color: Yellow-Green Group 144B.

*Petiole underside.*—Smooth, with prickles.

*Stipules.*—Short, serrated, about ¾ inch long.

*Disease resisance.*—Resistant to mildew, blackspot and rust under normal growing conditions at Albrighton, Wolverhampton, England.

Wood:

*New wood.*—Color: Greyed-Purple Group 183B and Yellow-Green Group 144A. Bark: Smooth.

*Old wood.*—Color: Yellow-Green Group 144A. Bark: Smooth.

Prickles:

*Quantity.*—On main canes from base: Ordinary. On laterals from main canes: Ordinary.

*Position.*—Quite evenly distributed up the stem.

*Form.*—Medium to short, hooked downward.

*Color when young.*—Greyed-Red Group 180B.

*Color when mature.*—Greyed-Orange Group 165A, but lighter.

Small prickles:

*Quantity.*—On main stalks: None. On laterals: Very few.

*Color.*—Greyed-Purple Group 184A.

I claim:

1. A new and distinct variety of shrub rose plant of the *Rosa hybrida* class, substantially as herein shown and described, characterized particularly as to novelty by the unique combination of its disease resistance; strong growth; pink blooms of an old-fashioned shape; and the ability to repeat flower well through the summer.

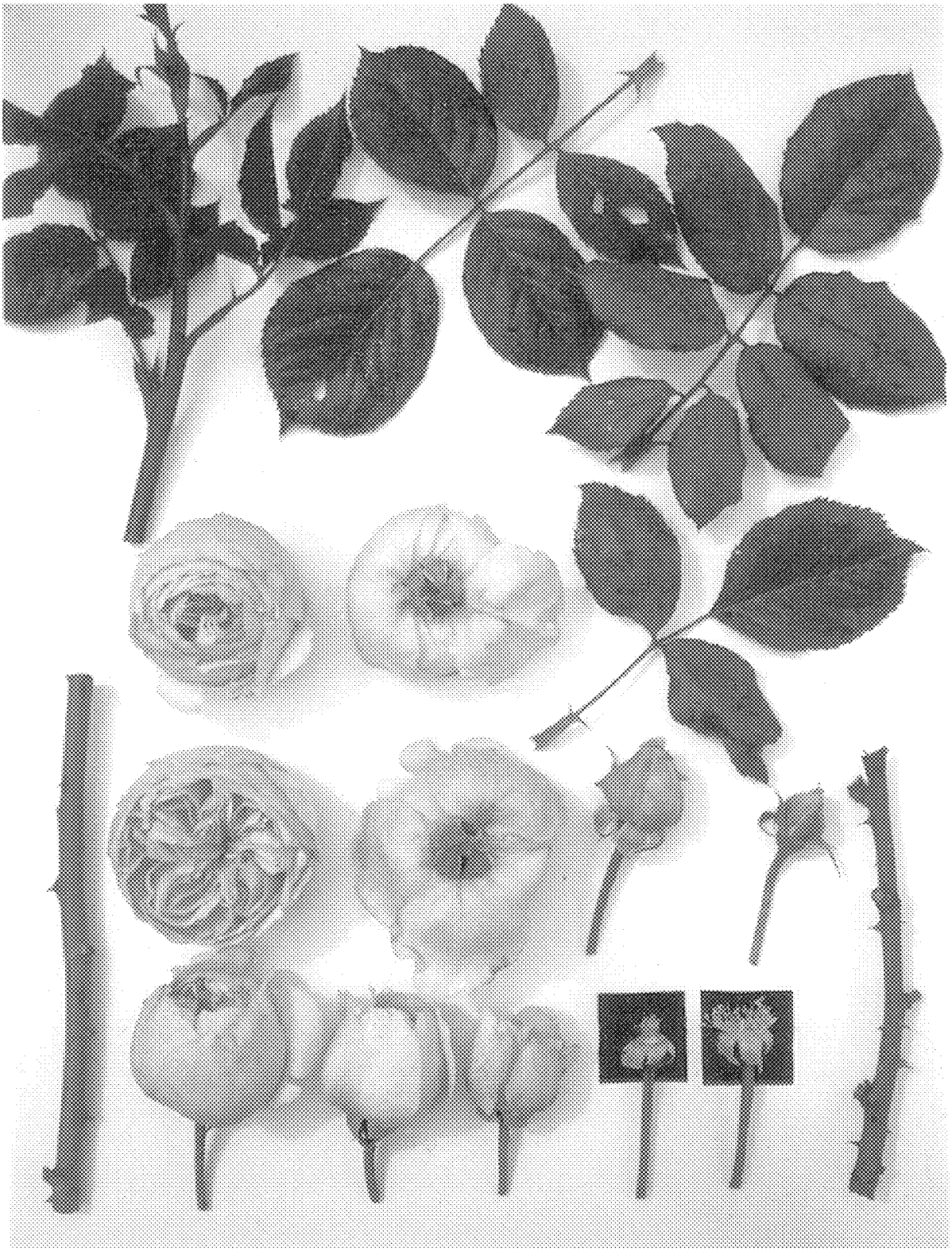

* * * * *